United States Patent
Biginton et al.

(10) Patent No.: US 10,668,297 B2
(45) Date of Patent: Jun. 2, 2020

(54) MAGNETIC STIMULATION (MS) COIL ARRANGEMENT

(71) Applicant: The Magstim Company Limited, Whitland (GB)

(72) Inventors: Matthew Paul Biginton, Whitland (GB); Gary Anthony Thomas, Whitland (GB)

(73) Assignee: The Magstim Company Limited, Whitland (GB)

( * ) Notice: Subject to any disclaimer, the term of this patent is extended or adjusted under 35 U.S.C. 154(b) by 703 days.

(21) Appl. No.: 15/324,301

(22) PCT Filed: Feb. 23, 2015

(86) PCT No.: PCT/GB2015/050509
§ 371 (c)(1),
(2) Date: Jan. 6, 2017

(87) PCT Pub. No.: WO2016/005719
PCT Pub. Date: Jan. 14, 2016

(65) Prior Publication Data
US 2017/0203117 A1    Jul. 20, 2017

(30) Foreign Application Priority Data

Jul. 7, 2014 (GB) .................................. 1412044.8

(51) Int. Cl.
*A61N 2/02* (2006.01)
*A61N 2/00* (2006.01)

(52) U.S. Cl.
CPC .............. *A61N 2/02* (2013.01); *A61N 2/006* (2013.01)

(58) Field of Classification Search
CPC .......... A61N 2/00; A61N 2/002; A61N 2/004; A61N 2/006; A61N 2/008; A61N 2/02
See application file for complete search history.

(56) References Cited

U.S. PATENT DOCUMENTS 6,179,770 B1 * 1/2001 Mould .................. A61N 2/006
600/13
6,491,620 B1 12/2002 Davey
(Continued)

FOREIGN PATENT DOCUMENTS

GB           2336544 A      10/1999
WO       WO 97/00639 A2     1/1997
(Continued)

OTHER PUBLICATIONS

International Patent Application No. PCT/GB2015/050509, International Preliminary Report on Patentability dated Jan. 10, 2017.
(Continued)

*Primary Examiner* — Carrie R Dorna
(74) *Attorney, Agent, or Firm* — Kilpatrick Townsend & Stockton LLP

(57) ABSTRACT

The present invention relates to a magnetic stimulation (MS) and preferably transcranial magnetic stimulation (TMS) coil arrangement designed for use as a placebo treatment. Accordingly, the purpose of the invention is to reduce or remove the effect of the magnetic field generated in use by a magnetic stimulation coil arrangement whilst the appearance presented remains as expected from a MS coil arrangement. The invention comprises a radially wound conductive element having a plurality of turns forming at least one winding. There is further provided at least one conductive magnetic field disrupting element at least partially positioned adjacent to the at least one winding for disrupting a magnetic field generated in operation by the at least one winding. The conductive magnetic field disruptive element accordingly attenuates the generated magnetic field beneath the coil arrangement.

30 Claims, 15 Drawing Sheets

(56) References Cited

U.S. PATENT DOCUMENTS

| | | | | |
|---|---|---|---|---|
| 7,087,008 B2* | 8/2006 | Fox | ............... | A61N 2/02 600/13 |
| 2001/0041917 A1 | 11/2001 | Holcomb | | |
| 2009/0163976 A1 | 6/2009 | Brockardt | | |

FOREIGN PATENT DOCUMENTS

| | | |
|---|---|---|
| WO | WO 2014/022236 A1 | 2/2014 |
| WO | WO 2016/005719 A1 | 1/2016 |

OTHER PUBLICATIONS

International Patent Application No. PCT/GB2015/050509, Written Opinion of the International Searching Authority dated Jan. 10, 2017.

International Patent Application No. GB1412044.8, Patents Act 1977: Search Report under Section 17 dated Jan. 20, 2015.

\* cited by examiner

MAGNETIC STIMULATION (MS) COIL ARRANGEMENT

The present invention relates to a magnetic stimulation (MS) and preferably a transcranial magnetic stimulation (TMS) coil arrangement whereby the object of the invention is to reduce the effect of the magnetic field generated.

Magnetic stimulating of neuromuscular tissue is well known and comprises a stimulating coil made up of one or more windings, each having a plurality of turns which may generate a succession of electrical discharge pulses producing magnetic pulses which further induce electrical signals in the tissue. Such a coil arrangement is disclosed in U.S. Pat. No. 6,179,770 where the magnetic stimulator generally comprises a charging circuit, a capacitor, a discharge control and a winding which is of a size and power rating appropriate for the generation of magnetic fields sufficient to cause stimulation of a body portion. The individual winding or plurality of windings may be size adapted to fit partly over the cranium of a human patient in many applications, as well as being used for stimulation of other body parts. The coil arrangement including windings acts as an inductor and when connected to a stimulator which includes the capacitor provides an input voltage to the inductor which creates a circuit that passes an out of phase, sinusoidal voltage and current through the Transcranial Magnetic Stimulation (TMS) winding. An intense sinusoidal magnetic field is formed near the winding and is used to stimulate neurons in patients for medical and research applications. An example of a coil arrangement is presented in FIG. 1 which shows a double winding coil arrangement presented without a covering that may suitably be positioned on a patient's cranium. The windings are made up of a single wound conductive element formed into the double winding configuration which is connected to the capacitor (not shown in FIG. 1).

Such TMS coil arrangements are used for medical and research applications and as such there is a requirement to provide a placebo or sham treatment for use in TMS investigation. As such, it is a requirement to create a TMS coil arrangement whereby a patient believes they are receiving TMS treatment however the actual treatment may be significantly reduced or removed in its entirety. Importantly, when used, TMS coil arrangements make a distinctive sound made by the coil through rapid deformation of the turns in each winding. It is therefore desirable to create a coil arrangement that provides the same sound but where the magnetic field produced is considerably lower in comparison to an active coil. Furthermore, it is desirable for the magnetic field to be strong enough to provide peripheral stimulation on the scalp in close proximity to the winding but zero or very little cranial stimulation further from the winding which further indicates authenticity of the treatment.

One of the most commonly used solutions for creating a sham or placebo TMS winding is to place a metal or ferromagnetic plate in between the patient and the TMS winding. Due to the intense magnetic fields produced by TMS windings however, ferromagnetic materials generally saturate or have to be thick to compensate. Metal plates have to be thick to avoid rapid heating and if placed too close to the winding can create excessive noise due to a repulsive force formed between the winding and plate during operation. Generally this solution requires a considerable gap between the TMS winding and the included plate. This is often greater than 5 mm. To make such a sham coil arrangement requires a redesign of packaging meaning that the resulting product becomes bulky and in addition is visibly different to an active TMS coil arrangement, meaning a patient is aware of the difference between a true operational coil arrangement that provides TMS treatment and a sham coil arrangement.

According to the aspects of the present invention there is a Magnetic Stimulation (MS) coil and preferably a transcranial magnetic stimulation (TMS) coil or arrangement which is capable of giving the appearance and audible perception of delivering a magnetic stimulation effect to a patient.

According to a first aspect of the present invention there is a magnetic stimulation (MS) coil arrangement comprising a radially wound conductive element having a plurality of turns forming at least one winding, the coil arrangement further including at least one elongate conductive magnetic field disrupting element at least partially positioned adjacent to the at least one winding for disrupting a magnetic field generated in operation by the at least one winding, the elongate conductive magnetic field disrupting element arranged to attenuate the generated magnetic field beneath the coil arrangement.

The elongate conductive magnetic field disrupting element is within the magnetic field generated by the winding(s). The elongate conductive magnetic field disrupting element is in close proximity to the at least one winding. The elongate conductive magnetic field disrupting element is adjacent but not in conductive communication with the winding. In operation the magnetic field produced by the winding and in particular the rate of change of magnetic field induces a current in the elongate conductive magnetic field disrupting element that runs in the opposite direction to that in the winding having an effect of a significant cancellation of the magnetic field produced by the coil arrangement in the volume of space around the coil and disrupting element. It will be realized by the skilled addressee that the field in the voids between the windings and disruptive element is intensified.

A significant advantage of such an arrangement is the ability to create a sham TMS coil arrangement without major modification to existing products and their exterior appearance, weight and sound produced is unaltered whilst significantly lowering the magnetic field output beneath the coil arrangement and thus transferred to the patient.

It will be appreciated that the magnetic field can be at least partially and preferably largely or mostly cancelled beneath the coil arrangement due to the induced eddy currents in the at least one elongate conductive magnetic field disrupting element. It is important, therefore, that the at least one elongate conductive magnetic field disrupting element is electrically conductive. It is further preferable that the elongate conductive magnetic field disrupting element if non-ferromagnetic. The effect of a ferromagnetic material is to enhance the magnetic field. It will be appreciated to the skilled addressee that a ferromagnetic material may also be conductive however if a conductive ferromagnetic material was utilised as the elongate conductive magnetic field disrupting element then the ferromagnetic properties would work in conflict with the conductive properties meaning the effect of field cancellation would be reduced.

In the present invention it is beneficial that cranial stimulation is substantially removed however peripheral stimulation of a patient's head is still achieved. This means that the patient believes that MS treatment is being applied without actually receiving or receiving minimal treatment.

The elongate conductive magnetic field disrupting element is preferably substantially non-magnetic. The elongate conductive magnetic field disrupting element is preferably positioned such that current is induced therein by the generated magnetic field. The magnetic stimulation coil arrangement is beneficially termed a sham or placebo magnetic stimulation coil arrangement.

The skilled addressee will realise that the magnetic field is increased or amplified between the winding and the disrupting element however elsewhere (i.e. particularly above and beneath the coil arrangement) the effect is to reduce or cancel the magnetic field.

The winding formed of a plurality of turns is beneficially disposed to lie generally in a common plane. The winding is, however, often flexible so that in use the at least one winding may accommodate the form of a patient, preferably the form of the cranium.

The at least one disrupting element is beneficially a loop. The loop is preferably closed and is preferably closed at the head of the coil arrangement but could from a closed loop once connected to the stimulator incorporating one or more of the charging circuit, capacitor and discharge control. The closed loop is beneficially provided at the head comprising the winding(s) for ease of manufacture. The loop may not essentially take the form of a ring and may take alternative configurations such as circular, elliptical, square, triangular, hexagonal, any polygon or may partially be any of these shapes. In some embodiments a combination may be utilised such as a substantially circular first disrupting element and a substantially elliptical second disrupting element.

The plurality of turns beneficially lie in a generally common plane, and the at least one disrupting element preferably lies at least partially in that plane. It has been found that positioning of the disrupting element in the generally common plane of the plurality of turns has a beneficial effect for reducing the magnetic field generated. The at least one disrupting element may be positioned outside the generally common plane in which the turns are positioned. In one embodiment a plurality of disrupting elements are provided which may be nested.

It is beneficial that first and second disrupting elements are provided. The number of windings and the polarity of adjacent windings has an implication in respect of the number of disrupting elements that provide a beneficial effect. In the event of provision of a single winding, it is beneficial to provide a first and second disrupting element. In the event of provision of a double winding, a first and second disrupting element have a significant effect, however, it is further beneficial to provide a third disrupting element. It will be appreciated that coil arrangements including more windings may be used, in which case additional disrupting elements are beneficially utilised.

At least one disrupting element beneficially comprises an inner disrupting element positioned adjacent to a radially inner edge of the at least one winding. At least part of the inner disrupting element is beneficially provided in the area which may be termed the core of the winding. The inner disrupting element is beneficially at least partially provided in the common plane in which the plurality of turns is disposed.

The radially inner or peripheral edge of the winding defines the core of the winding. It is beneficially substantially circular in shape. It is further beneficial that the inner disrupting element preferably substantially follows the contours of at least a portion of the radially inner peripheral edge. The at least one inner disrupting element is beneficially in close proximity to the peripheral edge. The disrupting element must be close enough to the winding so that as a current is passed through the turns of the winding a current in the opposite direction is induced in the disrupting element.

The inner disrupting element beneficially follows a majority of the radially inner edge of one or more of the at least one winding.

The at least one disrupting element beneficially comprises an outer disrupting element adjacent a radially outer edge of one or more of the at least one winding. It is beneficial that the outer disrupting element follows a majority of the radially outer edge of one or more of the at least one winding. Again it is beneficial that the outer disrupting element is disposed in the common plane in which the plurality of turns of the winding are disposed.

It is further beneficial that both an inner and outer disrupting element are provided.

The first and preferably the second disrupting element if provided is beneficially radially spaced by one or more turns of the winding.

At least one disrupting element may be positioned radially between adjacent turns of one or more of the at least one winding. From a manufacturing perspective it is easier, however, to provide a disrupting element either or in combination radially inwardly and/or radially outwardly of the winding however it is still possible and functionally effective to position a disrupting element radially between adjacent turns of one or more of the at least one winding.

The inner disrupting element is beneficially adjacent a radially inner edge and is beneficially in one embodiment a substantially solid element, meaning it is not a loop but effectively forms a solid plate. It has been determined that a current is induced in a disrupting element adjacent a radially inner peripheral edge irrespective of whether the disrupting element in this location is a loop or a solid element.

A neck portion beneficially extends from the winding having a connector for connection to a power source, the at least one disrupting element terminating before the connector. Preferably the at least one disrupting element is a loop and this terminates before the connector. It is beneficial to form the loop in the head of the coil arrangement where the loop is isolated from the connector and power source. It is however possible to arrange the TMS coil arrangement such that a loop is formed once the coil arrangement is attached to the power source. The power source may have therefore effectively complete the loop or may alternatively be arranged to optionally supply current through the loop once connected to the power source in the opposite direction to that in the winding as this will further achieve cancellation of opposing magnetic fields.

The radially wound conductive element is beneficially formed into first and second windings. In some embodiments additional windings are provided dependent on the area, body position and size of the person to be treated.

A first magnetic field disrupting element is preferably provided adjacent the first winding and a second magnetic field disrupting element is preferably provided adjacent the second winding. The first magnetic field disrupting element is beneficially adjacent a radially inner portion of the first winding and the second magnetic field disrupting element is preferably provided adjacent a radially inner portion of the second winding.

At least one magnetic field disrupting element is beneficially provided at least partially positioned adjacent the first and second winding. This magnetic field disrupting element is preferably elongate. It is beneficial that this elongate conducting magnetic field disrupting element extends adjacent a portion of the radially outer edge of the first winding and the radially outer edge of the second winding and it is beneficial that the elongate magnetic field disrupting element substantially surrounds a majority of the first and second windings.

The first magnetic field disrupting element beneficially extends adjacent a portion of the radially inner edge of the first winding, and the second magnetic field disrupting element beneficially extends adjacent a portion of the radially inner edge of the second winding, wherein the disrupting element positioned adjacent the first and second windings comprises a third conductive magnetic field disrupting element extending at least partially adjacent a radially outer edge of the first and second windings. The third disrupting element is preferably elongate. As such, if using two windings or a double winding configuration it is beneficial to provide three conductive magnetic field disrupting elements. The three magnetic field disrupting elements beneficially comprise two radially inner magnetic field disrupting elements and one radially outer magnetic field disrupting element that is positioned adjacent a radially outer edge of the first and the second windings. This is beneficial when utilising a reverse polarity (RP) coil arrangement. Alternatively, a first outer disrupting element is beneficially adjacent a radially outer edge of a first winding, and a second outer disrupting element is beneficially adjacent the second winding. This is particularly beneficial in an embodiment when modifying a standard TMS coil arrangement rather than providing a reverse polarity (RP) coil specifically designed as a sham or placebo treatment coil.

The plurality of turns of the first winding beneficially lie in a generally common first plane, and the individual outer elongate conductive magnetic field disrupting element lies at least partially in the first plane, and the second winding lies in a generally common second plane, and the individual outer elongate conductive magnetic field disrupting element lies at least partially in the second plane. It is beneficial that the first plane and second plane are substantially the same.

The turns of the radially wound conductive element are preferably wound clockwise or counter-clockwise for both the first and the second winding. This is beneficial as winding of turns in the same direction means that magnetic fields are provided in opposing directions meaning significant cancellation of these magnetic fields. This is a known technique in the art for producing sham coils however is not sufficiently effective to convince the patient that true treatment is being carried out. Without changing the power supplied to this coil it is hard to reduce the field sufficiently to prevent stimulation completely.

The at least one winding and at least one elongate conductive magnetic field disrupting element are beneficially provided in a housing. The housing may be a molded housing configured to receive the at least one winding and magnetic field disrupting element and retain these components in a pre-determined position and orientation. It will be further be appreciated, however, that the housing may be a potting material which is effectively molded around the at least one winding and conductive magnetic field disrupting element ensuring their relevant positions to each other and maintaining them in this fixed position.

According to a second aspect of the present invention there is a magnetic stimulation (MS) coil arrangement comprising a radially wound conductive element having a plurality of turns forming at least one winding, the coil arrangement further including a plurality of conductive magnetic field disrupting elements at least partially positioned adjacent the at least one winding for disrupting a magnetic field generated in operation by the at least one winding, the conductive magnetic field disrupting elements arranged to attenuate the generated magnetic field beneath the coil arrangement.

The plurality of turns preferably lie in a generally common plane, and the first and second disrupting elements beneficially lie at least partially in that plane.

The first and the second disrupting elements are beneficially radially spaced by one or more turns of the winding.

The first and optionally the second conductive magnetic field disrupting element is beneficially elongate.

The first and optionally the second conductive magnetic field disrupting element is beneficially a loop, and beneficially a closed loop.

The first conductive magnetic field disrupting element is beneficially adjacent a radially outer edge of the at least one winding.

The second conductive magnetic field disrupting element is preferably adjacent a radially inner edge of the at least one winding. The second conductive magnetic field disrupting element may be a plate.

It will be appreciated that advantages are identified and preferred features of the second aspect of the present invention may also be presented features of the first aspect of the present invention, and should be included as such.

According to a third aspect there is a magnetic stimulation (MS) coil arrangement comprising a radially wound conductive element having a plurality of turns in a substantially common plane forming at least one winding, the coil arrangement further including a conductive magnetic field disrupting element at least partially positioned adjacent the at least one winding and being at least partially disposed to lie in the substantially common plane for disrupting a magnetic field generated in operation by the at least one winding, the conductive magnetic field disrupting element arranged to attenuate the generated magnetic field beneath the coil arrangement.

It will be appreciated that benefits of the third aspect have corresponding benefits associated with the first and the second aspects. Further, preferred features of the third aspect are presented with respect to the first and second aspects.

In respect of the third aspect it is beneficial that in particular first and second conductive magnetic field disrupting elements are provided. The outer disrupting element is beneficially elongate and has been defined and described in detail above.

Also according to the present invention there is a method of attenuating the magnetic field generated in operation by a magnetic stimulation (MS) coil arrangement comprising a radially wound conductive element having a plurality of turns forming at least one winding and an elongate conductive magnetic field disrupting element positioned at least partially adjacent to the at least one winding, and passing a current through the at least one winding, wherein the elongate conductive magnetic field disrupting element attenuates the magnetic field beneath the MS coil arrangement.

Aspects of the present invention will now be described by way of example only with reference to the accompanying drawings in which:

FIG. 1 is a schematic perspective view of a known coil arrangement represented in two forms wherein FIG. 1(a) also shows the direction of current flow through the two windings and FIG. 1b shows the conductive element that connects to the TMS system.

FIG. 2 is a schematic plan view of a double winding coil arrangement showing in FIG. 2(a) a normal coil arrangement, and in FIGS. 2(b), 2(c) and 2(d) showing a coil arrangement according to exemplary embodiments of the present invention. FIG. 2(e) shows a known reverse polarity (RP) coil arrangement as known in the art and FIGS. 2(f), 2(g) and 2(h) show coil arrangements according to exemplary embodiments of the present invention.

FIG. 3 is a schematic graphical representation of the peak rate of change of magnetic field near the centre of a winding for a normal coil and a reverse polarity coil and also according to exemplary embodiments of the present invention presented in FIG. 2.

FIG. 4(a) is a finite element model showing the peak magnetic field comparing normal and reverse polarity coil arrangements in comparison to the magnetic field modelled for coil arrangements according to exemplary embodiments of the present invention through application of a 100% stimulator voltage, and FIG. 4(b) is a comparison of the peak magnetic field with the stimulator voltage reduced to compensate for the noise produced attributable to the at least one disruptive element compared to the peak magnetic field associated with a normal (non-reverse polarity) coil arrangement.

Figure 7:
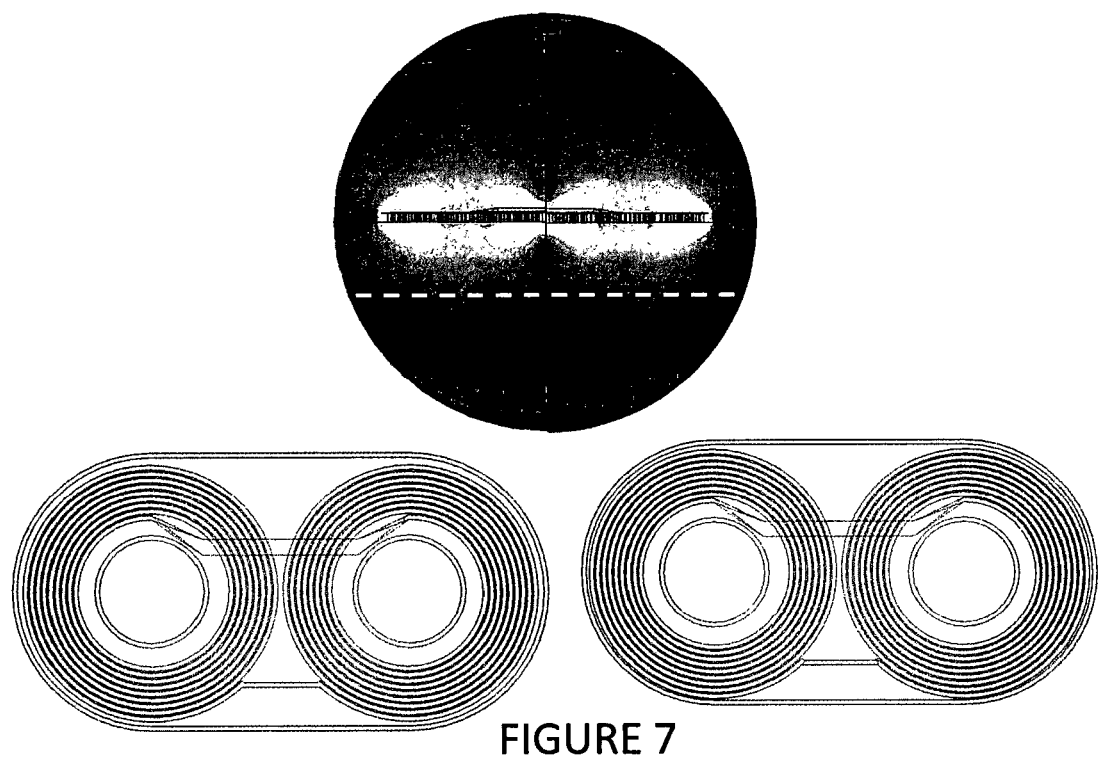

FIG. 7 is a schematic plan view and accompanying peak magnetic field representation provided from finite element method modelling for an embodiment of a coil arrangement according to an exemplary embodiment of the present invention. In FIG. 7 a comparison is made between relative positions of an elongated conductive magnetic field disrupting element, with an outer disrupting element shown further away from the windings on the left hand side.

Figure 8:
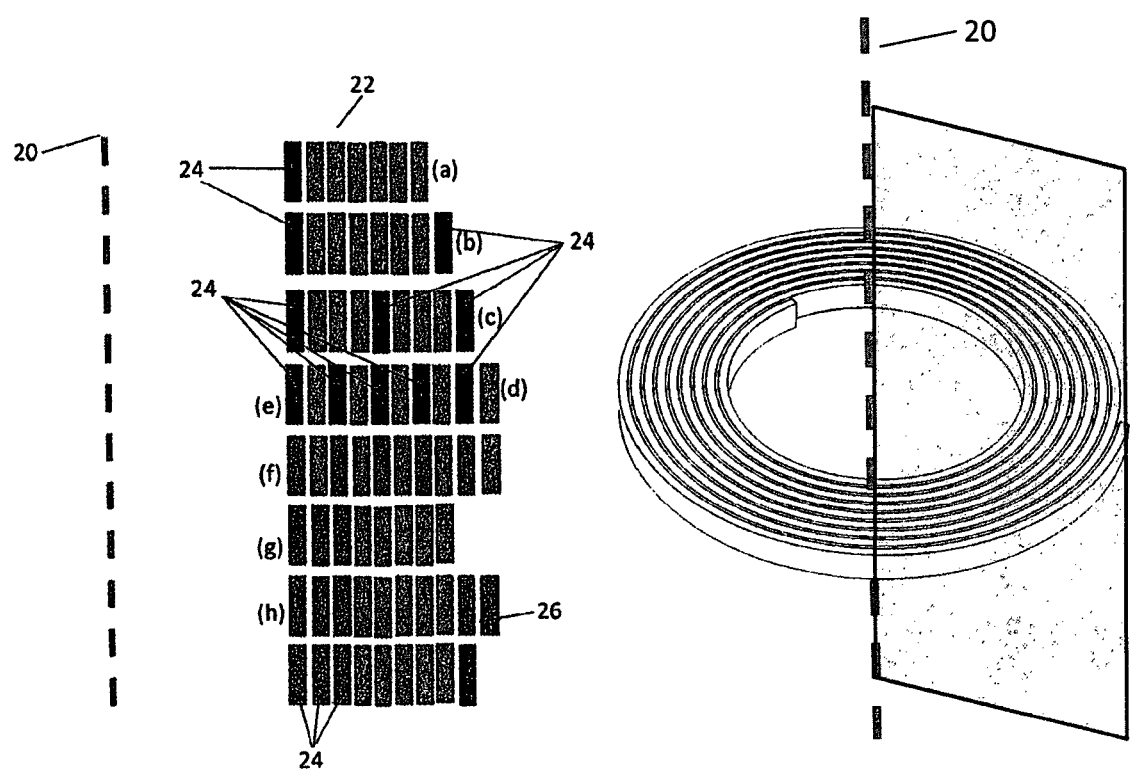

FIG. 8 is a schematic cut through of a single winding according to an exemplary embodiment of the present invention.

Figure 9:
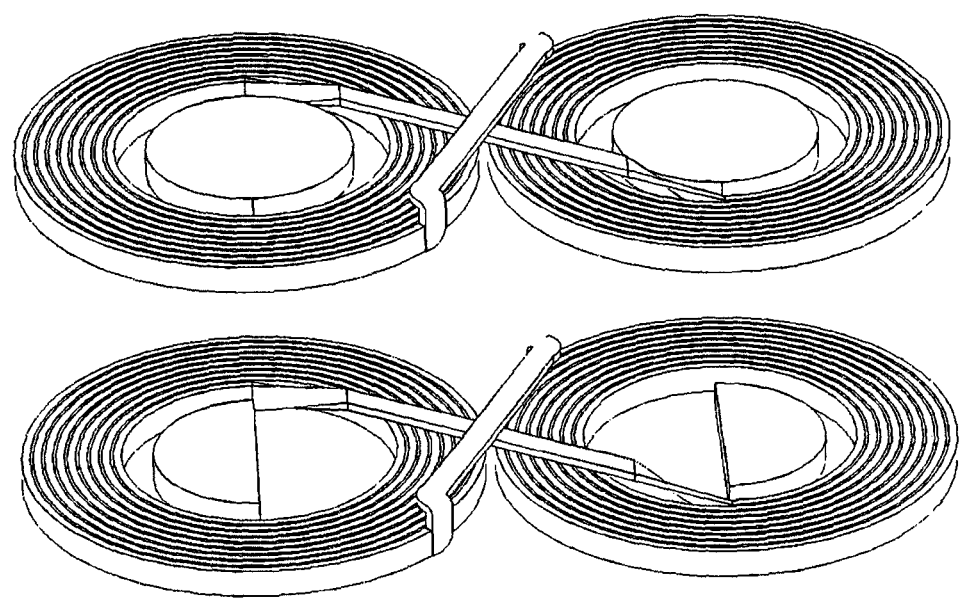

FIG. 9 is a schematic representation of two different plan views of coil arrangements according to exemplary embodiments of the present invention.

Figure 10A:
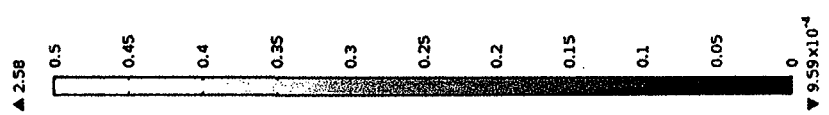
Figure 10A:
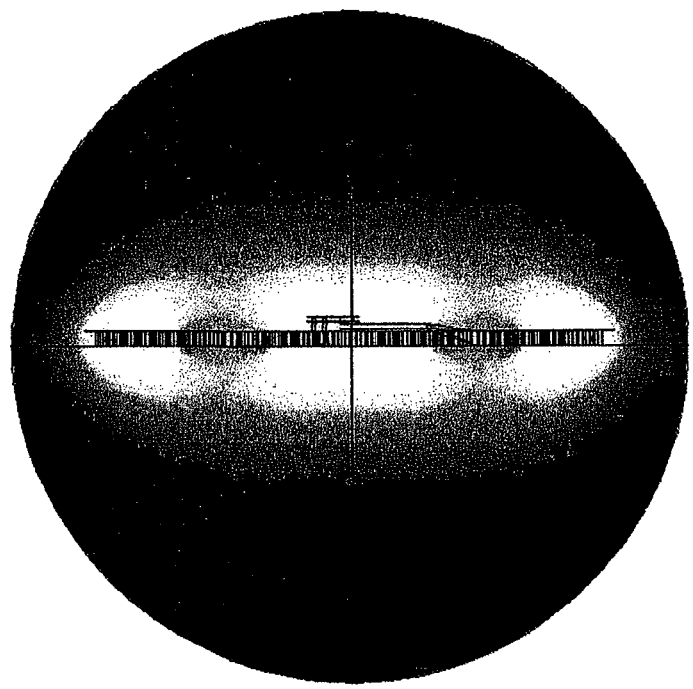
Figure 10B:
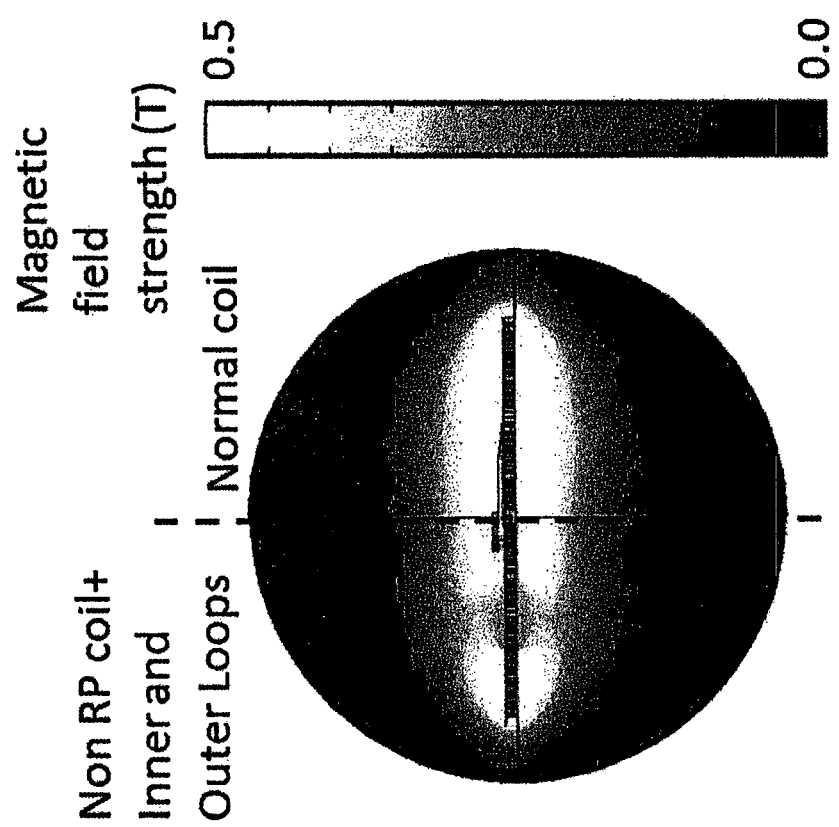

FIG. 10(a) is a presentation of the peak magnetic field from finite element method modelling showing the peak magnetic field of a normal polarity coil arrangement with two windings as represented in FIG. 2(d) and FIG. 10(b) shows on the left hand side of the comparative finite element method modelling the peak magnetic field as shown in FIG. 10(a) and on the right hand side compares this to the peak magnetic field with a normal coil arrangement.

FIGS. 11(a) and (b) show a plan view and perspective view respectively of a single winding coil arrangement according to an exemplary embodiment of the present invention.

Figure 11:
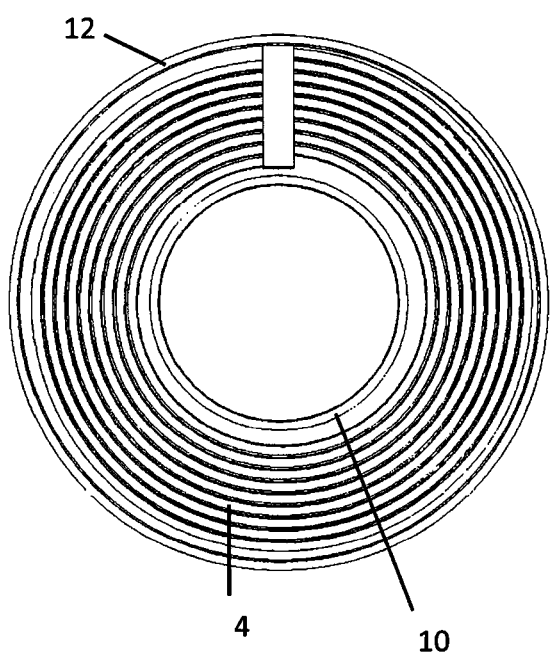
Figure 11:
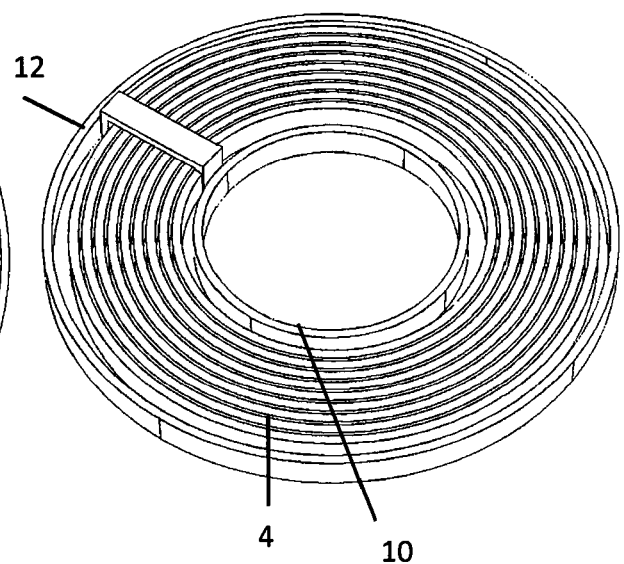
Figure 11C:
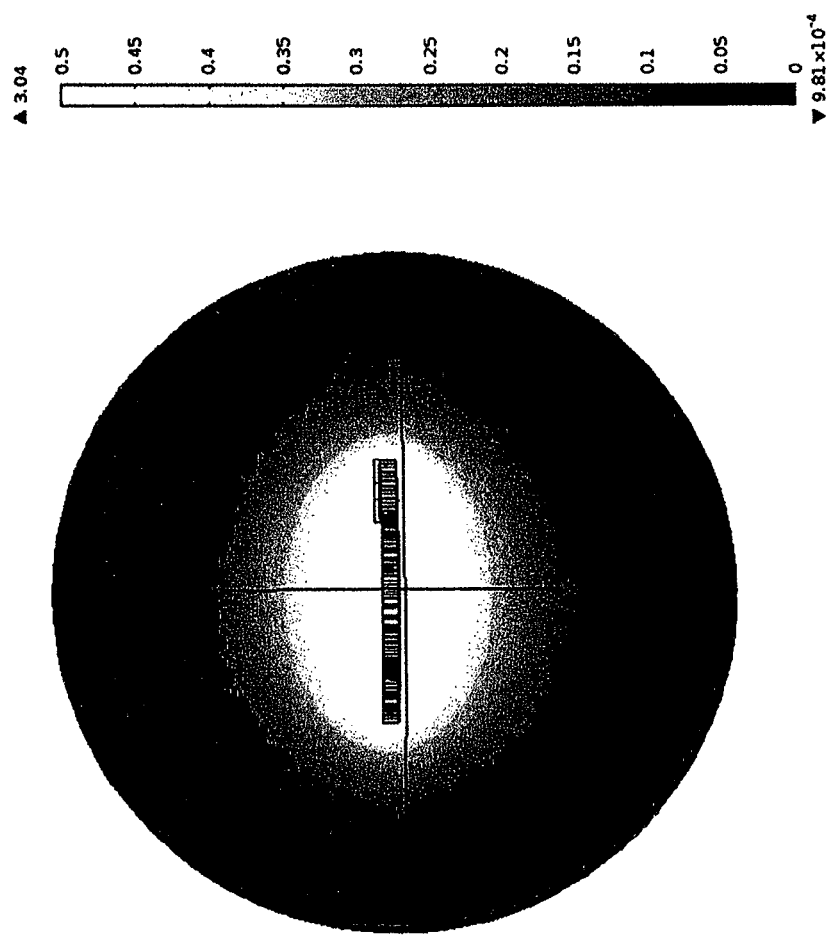

FIG. 11(c) is a finite element method modelling of a normal coil arrangement with a single winding giving a representation of the peak magnetic field associated with such a coil arrangement.

Figure 11D:
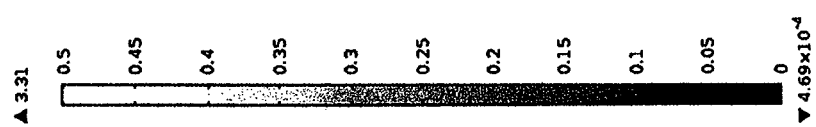
Figure 11D:
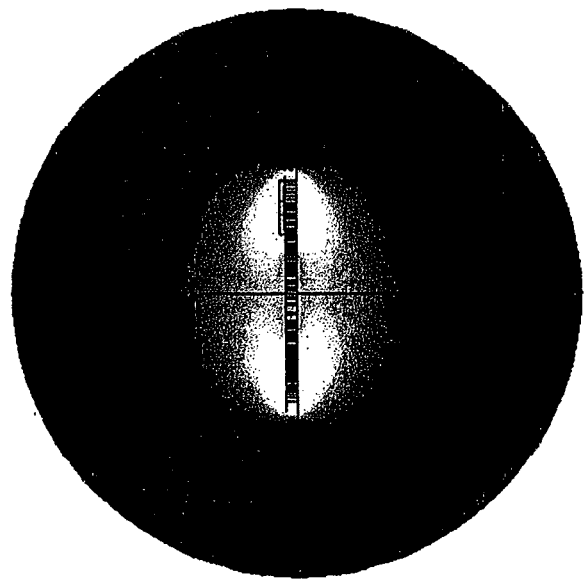

FIG. 11(d) presents the peak magnetic field associated with a coil arrangement having a single winding according to an exemplary embodiment of the present invention.

Figure 11E:
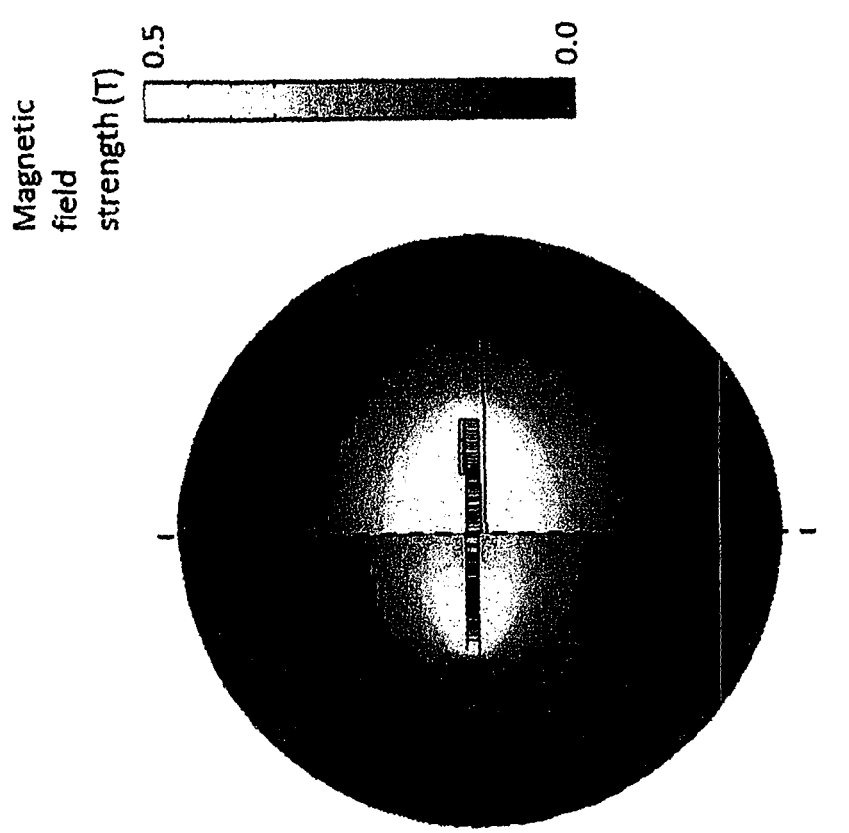

FIG. 11(e) is a comparison between the peak magnetic field associated with a normal coil arrangement of single winding (right hand side) and a coil arrangement with a single winding including inner and outer disrupting elements (left hand side).

Figure 12:
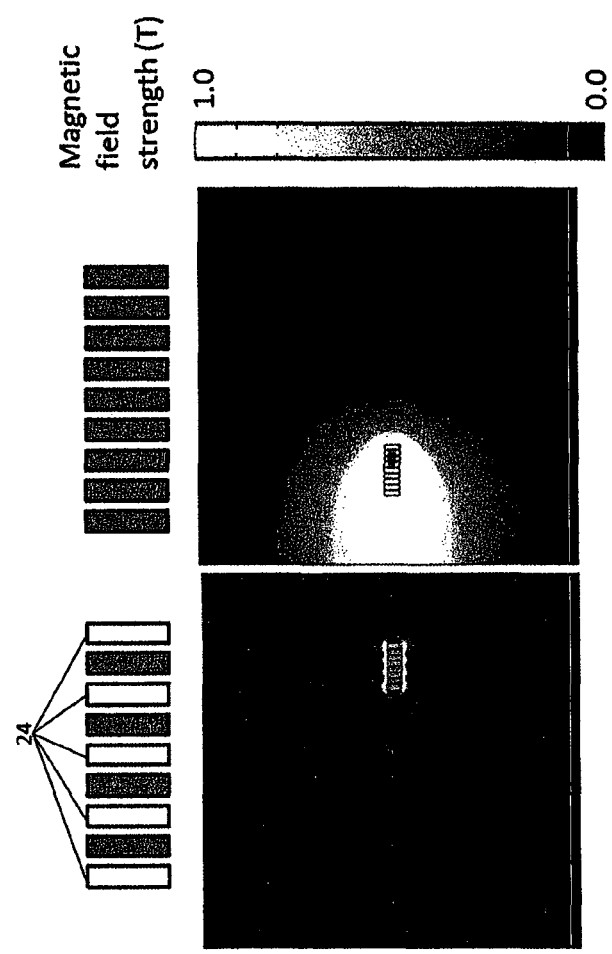

FIG. 12 is a comparison between the peak magnetic field associated with a normal coil arrangement represented on the right hand side and a coil arrangement according to an exemplary embodiment incorporating conductive disrupting elements dispersed radially between the turns of the winding in an embodiment shown for example in FIG. 8(f) utilising a plurality of individual disrupting elements.

Figure 13:
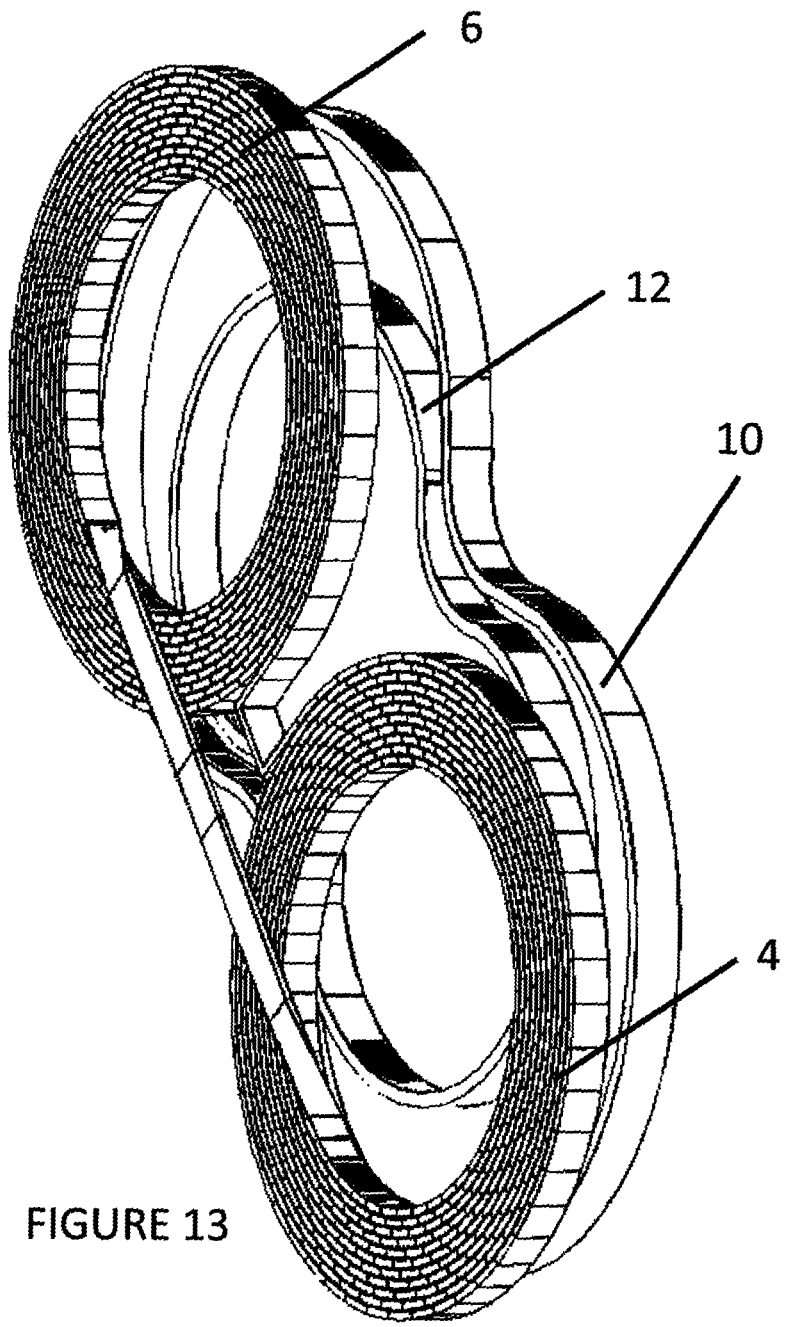

FIG. 13 is a schematic perspective representation of further exemplary embodiment of the present invention.

Figure 14:
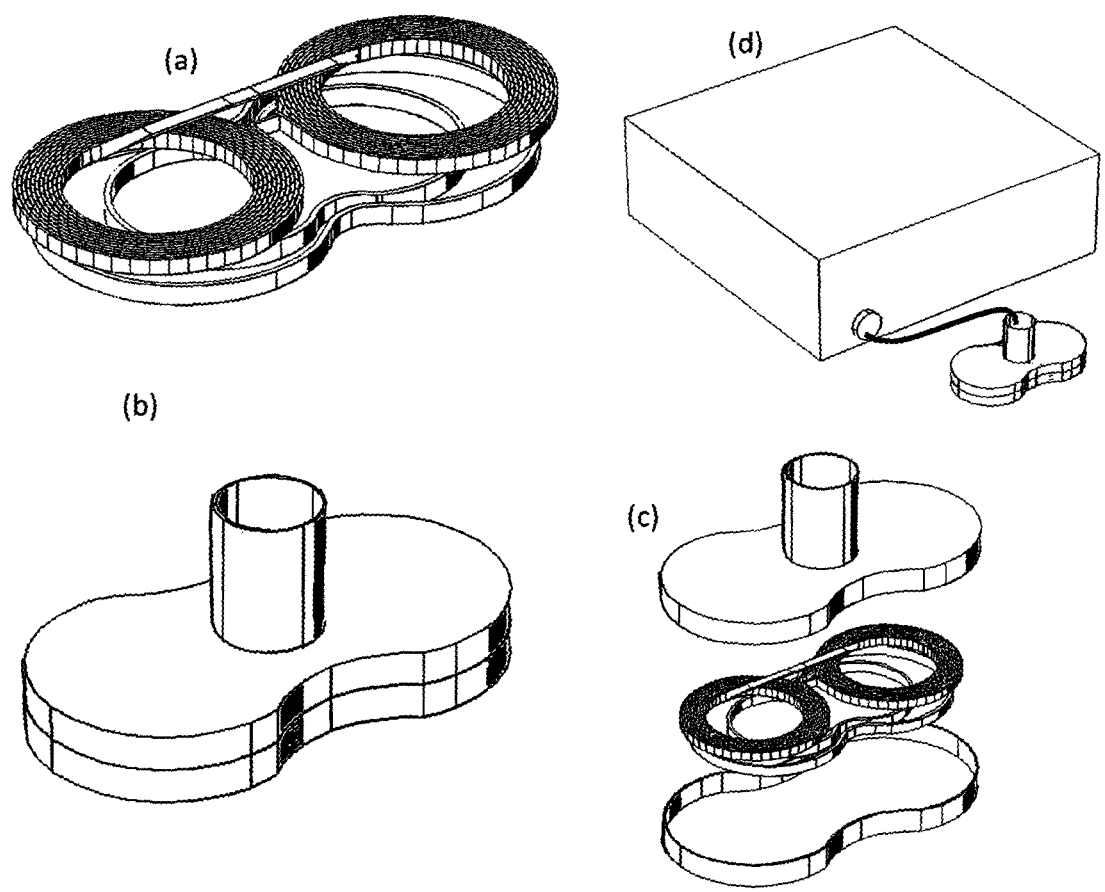

FIG. 14a is a presentation of the arrangement of FIG. 13. FIG. 14b is a schematic presentation of a housing for accommodating the at least one winding and at least one elongate conductive element. FIG. 14c is an open view of the housing comprising the two part structure which engage to accommodate the at least one winding and at least one elongate conductive disrupting element. FIG. 14d is a presentation of a magnetic stimulation coil arrangement within the housing in communication with the stimulation apparatus.

Referring to FIG. 1(a) there is a prior art normal coil arrangement used for TMS treatment. The arrows indicated in FIG. 1(a) identify the direction in which the current travels through the coil arrangement and the turns of the winding at an instant in time. It will be appreciated that the first winding 4 is wound radially outwardly to inwardly and extends via a bridge portion 5 to a second winding 6 comprising a plurality of turns which is wound in the opposing direction, radially inwardly to radially outwardly. As shown in FIG. 1(b), the first and second windings 4, 6 are formed of a single elongate conductive element which extends by having neck 10 to a stimulator including power source (not shown). The power source is incorporated into a stimulator and includes a capacitor that provides an input voltage which resonates passing an out of phase sinusoidal voltage and current through the first and second windings 4, 6. An intense sinusoidal magnetic field is formed near the winding that is used to stimulate neurons in patents for medical and research applications.

Figure 1:
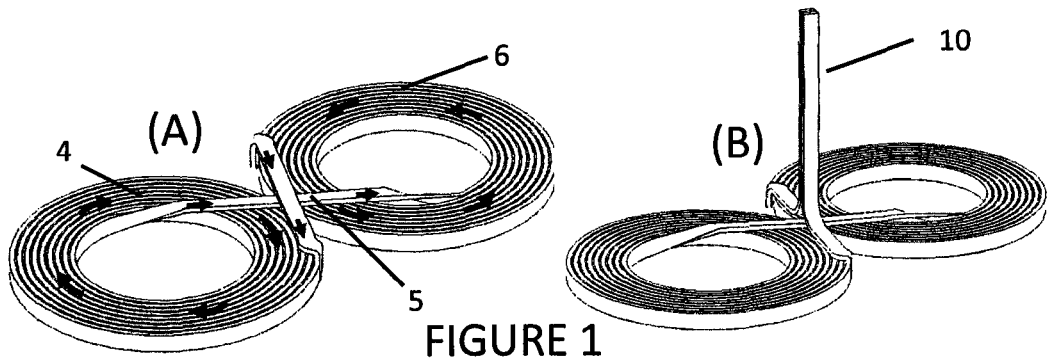
Figure 2:
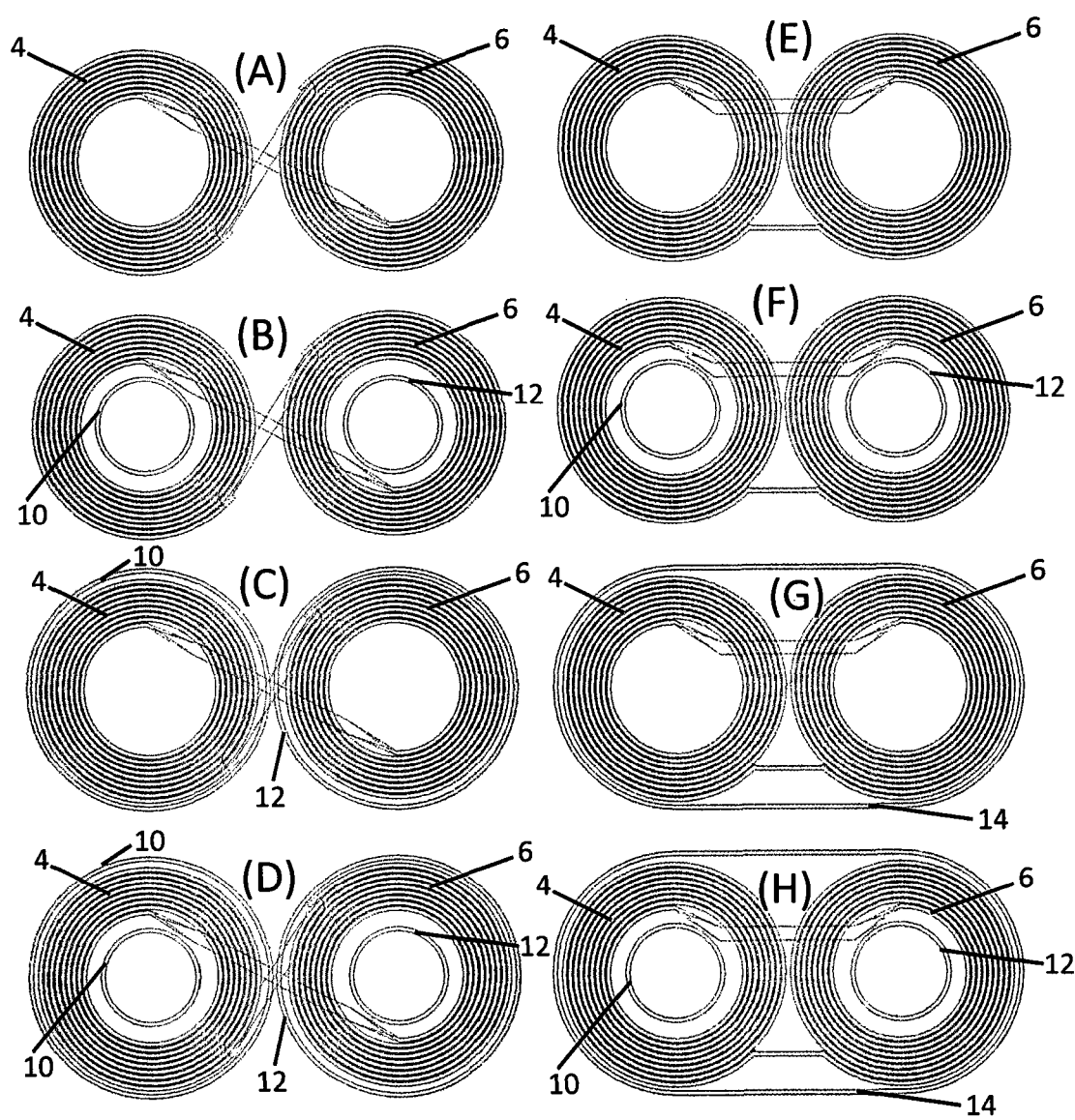

Referring to FIG. 2 different embodiments of the present invention are presented whereby FIG. 2(a) is the same coil arrangement comprising first and second windings as presented in FIG. 1. FIGS. 2(b), (c) and (d) show the same windings whereby the current flows in opposing clockwise and counter-clockwise directions through the first and second windings 4, 6 respectively. In FIG. 2(b) an embodiment according to the present invention is presented showing a first and second elongate conductive magnetic field disrupting element 10, 12 respectively positioned radially inwardly of the innermost turn of each of the first and second windings. The disrupting elements 10, 12 are in close proximity to the windings 4, 6 however are not in conductive communication. The disrupting elements 10, 12 are disposed at least partially in the common plane of the turns of the first winding 4 and the second winding 6. It will be appreciated, however, in certain embodiments that the turns of the first winding 4 and the turns of the second winding 6 are in different planes, meaning the disrupting elements 10, 12 may be in different relative planes. It will be further appreciated that the turns of the windings 4, 6 are deformable meaning may deform or deflect to accommodate the contours of each patient.

Referring to FIG. 2(c), a first 10 and a second 12 disrupting element are provided around the peripheral edge of a majority of the first and second windings 4, 6. Again, it is beneficial that the disrupting elements 10, 12 are at least partially disposed in the generally common plane of each of the first and second windings 4, 6 respectively. It will further be appreciated that each of the disrupting elements 10, 12 are in close proximity to the windings but are not in conductive communication.

Referring to FIG. 2(*d*), in this embodiment disrupting elements have been provided incorporating all of the disrupting elements presented in FIGS. 2(*b*) and 2(*c*) and their relative positioning.

The rate of change of magnetic field produced by the first and second windings 4, 6 induces currents in the disrupting elements 10, 12 that run in the opposite direction to the current in the turns of the windings. The result is a large cancellation of the magnetic field produced by the coil arrangement. It will be further appreciated that as described with respect to FIG. 8 alternative configurations of the disrupting elements may provide similar magnetic field cancelling effects such as positioning between adjacent turns. Although this is effective in respect of magnetic field cancelling, manufacturing is more difficult. It is beneficial that the embodiment described in FIGS. 2(*b*), (*c*) and (*d*) enable the creation of a sham coil arrangement without major modification to an existing product and its appearance. Furthermore, the weight and sound produced during the operation is very similar to a functioning TMS coil arrangement whilst significantly lowering the output magnetic field and power used to operate the sham coil.

The sound produced during operation using 100% stimulator voltage causes a significant increase in the sound when using the disrupting element or elements. As such it is beneficial to scale the voltage downwardly meaning that the sound produced is reduced to approximately the same level as with the output of a normal coil arrangement. This has the further beneficial effect of reducing the peak magnetic field which will be demonstrated with respect to FIG. 4(*b*).

At this point it should further be appreciated that it is possible to provide a single winding also according to the present invention, as described with respect to FIGS. 10 and 11 for example.

Referring now to FIG. 2(*e*) there is presented a reverse polarity (RP) coil arrangement used in the art as a sham coil. The current flowing in each winding run in opposing directions and as such where the first and second windings 4, 6 are in close communication the magnetic field is effectively significantly reduced, however complete lack of stimulation is difficult to achieve using the RP method alone. The same reverse polarity (RP) coil arrangement is presented in FIGS. 2(*f*), 2(*g*) and 2(*h*) effectively utilising different field disrupting elements to achieve improved magnetic field cancellation. In FIG. 2(*f*) the first and second disrupting elements 10, 12 are provided positioned in a similar manner to as described with respect of FIG. 2(*b*). In FIG. 2(*g*) a single disrupting element 14 is provided extending around a majority of the peripheral edge of the windings. A continuous loop comprising the disrupting element 14 is positioned around the peripheral edge of the two windings 4, 6 which is not available for the normal coil arrangement and embodiment thereof as described with respect of FIGS. 2(*a*) to 2(*d*) due the fact that in these embodiments current induced in such a loop would cancel. The arrangement of FIG. 2(*g*) is particularly beneficial from a manufacturing perspective as it enables the winding(s) to be manufactured and the disrupting element 14 to be positioned around the windings.

With respect to FIG. 2(*h*) further improvements to the magnetic field cancelling effect has been found through the incorporation of additional disrupting elements 10, 12.

Figure 3:
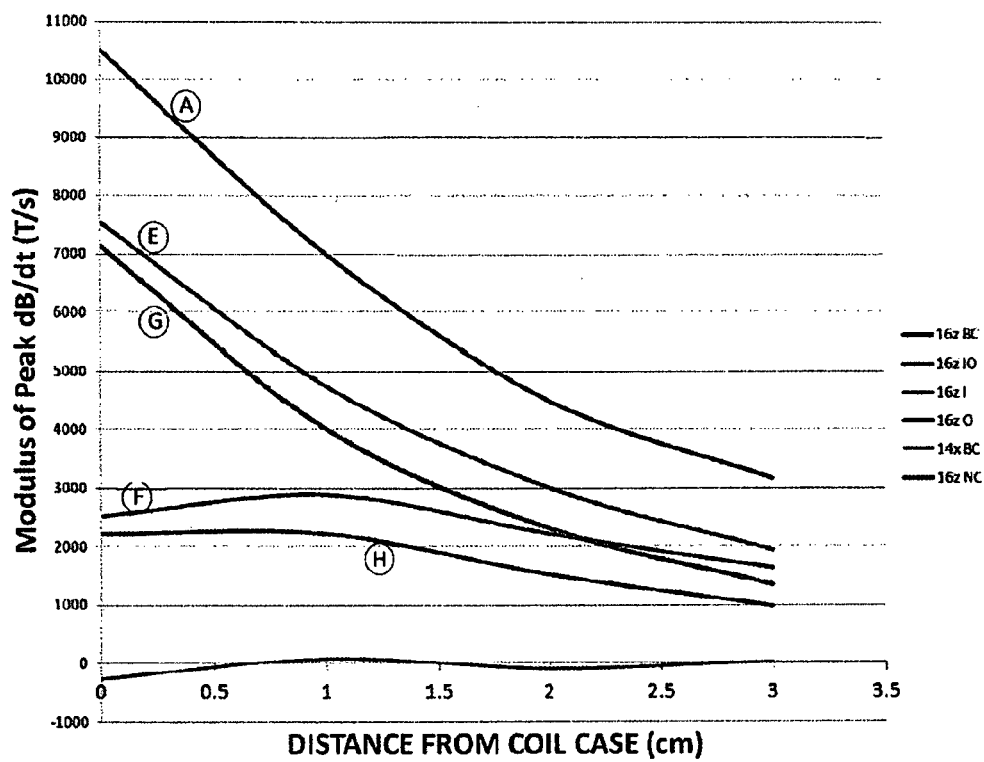

The voltage induced in the brain for TMS is related to the rate of change of magnetic field. FIG. 3 shows experimental data of absolute peak rate of change of magnetic field near the centre of one of the windings for a normal coil arrangement (FIG. 2(*a*)), a RP coil arrangement (FIG. 2(*e*)), a RP coil arrangement with a disrupting element around the perimeter of the windings (FIG. 2(*g*)), a RP coil arrangement with disrupting elements within the winding cores (FIG. 2(*f*)), and a combination of the central (inner) and perimeter (outer) disrupting elements (FIG. 2(*g*)). The reverse polarity coil arrangement of FIG. 2(*e*) has a peak dB/dt that is about 26% less than normal coil windings (FIG. 2(*a*)) at a depth of 3 cm away from the outer casing of the coil windings. This on its own is insufficient to prevent cranial stimulation. It should be noted that these comparisons have been made at the same unscaled voltage, which is scaled in operation of the present invention in order to reduce the sound generated to a level similar to that produced by a normal TMS coil arrangement.

If the inner disrupting elements are added to the RP windings (FIG. 2(*f*)) a very large drop in dB/dt is observed close to the coil windings but at 3 cm this difference becomes marginal compared to the bare RP coil as presented in FIG. 2(*e*).

If the inner disrupting elements are added to the RP windings (FIG. 2 (*f*)) a very large drop in dB/dt is observed close to the coil windings but at 3 cm this difference becomes marginal compared to the bare RP coil of FIG. 2 (*e*).

If the outer disrupting element is added to the RP coil windings (FIG. 2 (*g*)) a small drop in dB/dt is observed close to the coil windings but this surpasses that of the inner loop at 3 cm.

If both inner and perimeter disrupting elements (FIG. 2(*h*)) are added a considerable drop in dB/dt is observed both close to the coil and at 3 cm away from the coil. A 63% reduction in dB/dt is observed on comparison to the bare normal coil windings of FIG. 2(*a*). For completeness the decay of the x component of the magnetic field at the centre of the two coils is also show for the bare RP windings of FIG. 2(*e*) in FIG. 3.

Figure 4A:
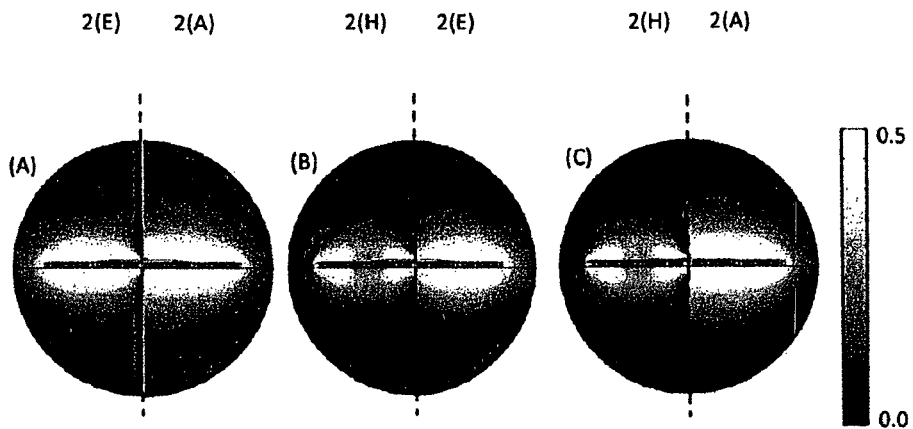

FIG. 4(*a*) is in comparison of the peak magnetic field shown on a saturated scale from finite element method modelling for different embodiments presented in FIG. 2 at the same power levels. Presented is effectively a cross section through a double winding where in order to aid comparison the peak magnetic field is presented for different windings on opposing sides of the vertical axis. FIG. 4(*a*) shows a comparison between the winding of FIG. 2(*e*) comprising a reverse polarity coil arrangement on the left hand side of the vertical axis against the peak magnetic field associated with a normal coil arrangement as presented in FIG. 2(*a*). It is clear that the reverse polarity winding has a faster decaying magnetic field than a normal polarity winding.

Figure 4B:
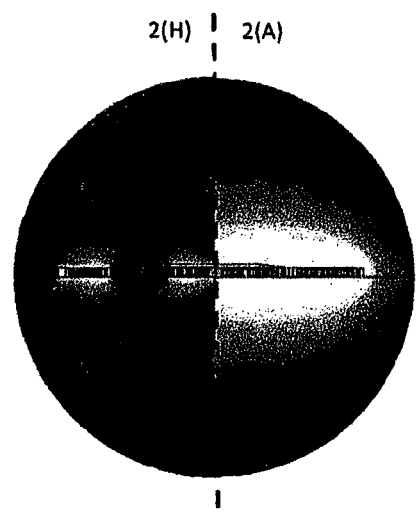

Referring to FIG. 4(*b*) the left hand side of the vertical axis presents half of the windings as presented in FIG. 2(*h*). The right hand side of the vertical axis presents the peak magnetic field associated with the reverse polarity coil of FIG. 2(*e*). It is clear that the reverse polarity winding with both inner and outer disrupting elements has much faster decaying fields than a standard reverse polarity winding. It is important to note that the light area showing high magnetic field projects to a depth of approximately 2 cm in the arrangement of FIG. 2(*h*). This is important as the skull is approximately 7 mm thick meaning that minimal magnetic field passes through the skull. This means that a patient will feel the effect of receiving physical contact with the coil arrangement and stimulation of nerves with minimal magnetic stimulation. It is noted, however, that further reduction of the magnetic field is achieved by reduction in the stimulator voltage, as represented in FIG. 4(b).

FIG. 4(c) presents on the left hand side of the vertical axis the peak magnetic fields associated with the windings of FIG. 2(h) and on the right hand side of the vertical axis shows the peak magnetic field in direct comparison to a normal double winding as presented in FIG. 2(a). The difference in peak magnetic field and the depth that the magnetic field can extend to is significantly reduced.

Referring now to FIG. 4(b) presented as a comparison between the peak magnetic field associated with a normal coil shown at 2(a) on the right hand side and on the left hand side is the peak magnetic field associated with the coil arrangement as presented in 2(h). However as previously described due to the noise produced attributable to the at least one disruptive element the stimulator voltage has been reduced to compensate for the sound produced. A similar sound to a normal TMS coil arrangement in operation is achieved through scaling of the stimulator voltage to approximately 35% meaning that the associated peak magnetic field is significantly reduced. This is beneficial as the magnetic field is massively reduced however the patient will feel some surface stimulation on the scalp. It will be noted, however, that the voltage scaling will be dependent upon the number of turns of a winding and the power settings and as such is controlled dependent on these features.

Figure 5:
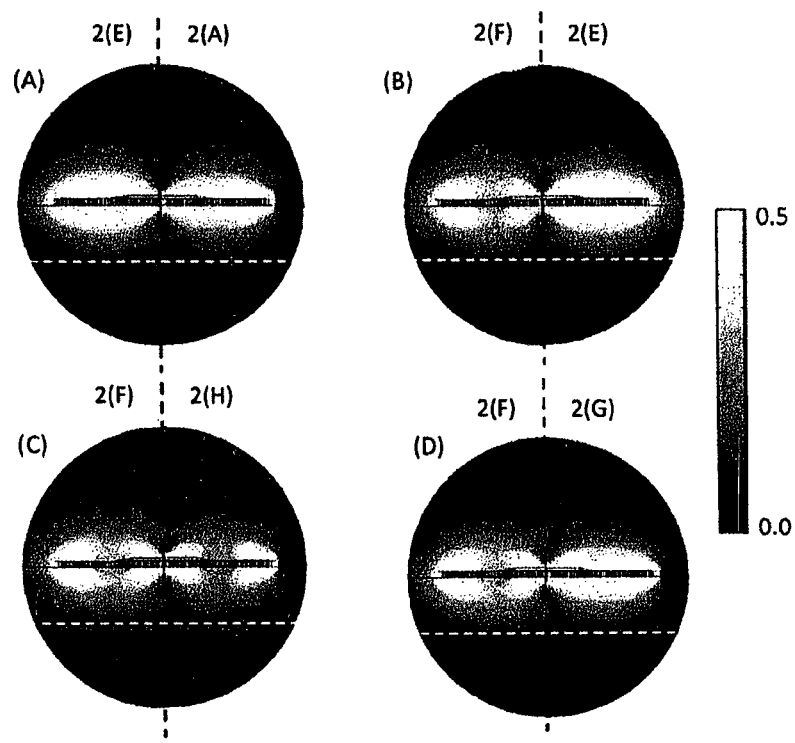
FIG. 5 is a comparison of the peak magnetic field from finite element method modelling comparing the magnetic field of a reverse polarity coil arrangement with coil arrangements according to exemplary embodiments of the present invention.

Now referring to FIG. 5 there are further presentations showing how the magnetic field strength (T) changes dependent on the relative positioning of the disrupting element or elements. FIGS. 5(a), 5(b) and 5(d) show that the coil arrangement of FIG. 2(g) has faster decaying fields than the bare RP coil of FIG. 2(e) and the coil arrangement of FIG. 2(f). FIG. 5(a) also shows that the arrangements of FIG. 2(g) also shows significant magnetic field decay compared to a bare RP winding arrangement of FIG. 2(e).

FIG. 5(b) shows the arrangement of FIG. 2(f) causes significant magnetic field cancellation close to the winding but little difference on comparison to the bare RP coil of FIG. 2(e) at further distances from the winding.

FIG. 5(c) shows that the arrangement of FIG. 2(h) which effectively incorporates the arrangements of FIGS. 2(f) and 2(g) increases both field cancellation close to and further from the windings. As it is sometimes desirable to have peripheral stimulation on or near the skin but very little or zero cranial stimulation (far) from the windings it is possible to tune both near and far stimulation dependent on the arrangements shown.

The sound produced from the coil arrangement as presented in FIG. 2(h) is generally louder than a normal coil arrangement shown, for example in FIG. 2(a). As such to correct this a reduction in winding(s) voltage may be artificially introduced through software to reduce the noise as previously described and best represented in FIG. 4(b) which has the added benefit of decreasing the field strength even further below the stimulation threshold.

Figure 6:
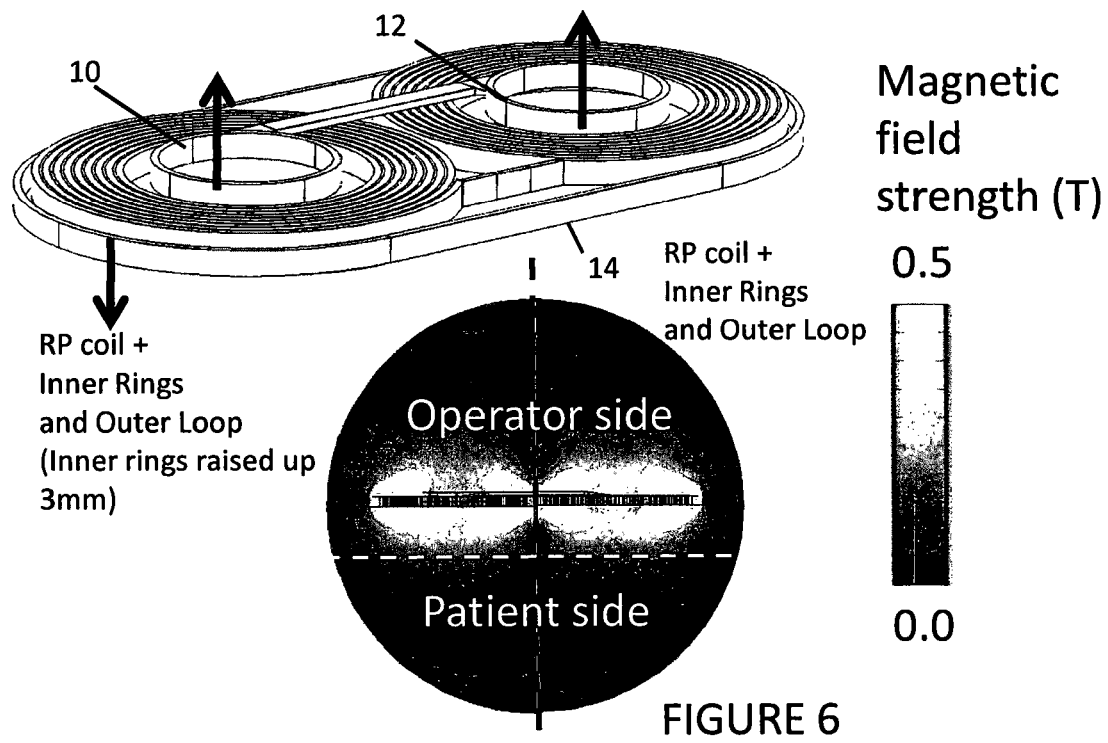
FIG. 6 is a schematic perspective view and accompanying peak magnetic field representation from finite element method modelling for an exemplary embodiment of the present invention.

It has further been determined that the magnetic field may be tuned dependent on specific requirements. For example, as illustrated in FIG. 6 the disrupting elements 10, 12, 14 may be moved as identified by the arrows partially outside the generally common plane of the one or more windings. By shifting the inner disrupting elements 10, 12 upwards or away from the patient it is possible to cancel the (near) fields less on the patient's side. By moving the outer disrupting element(s) downwards towards the patient it is possible to cancel the (far) magnetic field more on the patient's side thus lowering cranial stimulation but increasing peripheral stimulation. The effect of shifting the central or inner disrupting elements 3 mm upwards is shown in the magnetic field map presented in FIG. 6. By lifting up the inner disrupting elements the field cancellation on the operator's side has an increase whereas the field cancellation on the patient's side has decreased. It is noted, however, that only the magnetic fields close to the windings have seen a significant increase. Therefore, shifting the disrupting elements provides a method for tuning both the magnetic fields closer to the windings and the magnetic fields further away from the windings almost independently. This is a significant advantage for a sham coil arrangement as it is often desirable to provide little or no cranial stimulation on the scalp but retaining some surface feeling on the scalp.

It will be appreciated that again the schematic representation is for a double winding however the effect is equally present in a single winding utilising the inner and outer disrupting elements. However an alternative method to tuning the amount of magnetic field cancellation is to increase or decrease the size of the one or more disrupting elements. FIG. 7 demonstrates this principle by making the outer disrupting element smaller, or as presented in FIG. 7 by making the outer diameter less. Since the magnetic field is larger closer to the windings, by making the outer disrupting element smaller or in other words making the outer disrupting element closer to the windings. A larger dB/dt and the subsequent induced current generated in the outer disrupting element (due to its closer proximity to the winding) a greater magnetic field cancellation is observed. This presents another method for tuning by changing the gap between the inner disrupting element and the windings by reducing the radius of the inner disrupting elements and also decreasing the gap from the peripheral edge of the winding to the outer disrupting element to simultaneously decrease the magnetic fields further from the winding and increase the magnetic field closer to the winding which may be used for peripheral stimulation.

It is further noted that a similar magnetic field cancellation effect can be created by having disrupting elements below, above or a combination of both the windings instead of the provision of the disrupting element nested within the windings. As such the disrupting elements may be moved out of the generally common plane occupied by the turns of the windings.

Again it is noted that the aforementioned ideas and concepts can be equally applied to a single winding rather than a double winding system.

Referring now to FIG. 8 there is a cross section through a winding which has a plurality of turns where the dashed line 20 represents the axial symmetry line of the centre of the winding and the individual rectangles 22 represent a cross section through the turns of the windings. Each of the windings (a) to (h) represent alternative variations in the configuration of the windings. As presented in a, b, c and d a single disrupting element 24 may be wound, however individual disrupting elements may be provided. Clearly these have been presented by way of example only. There may alternatively be individual or single disrupting elements in non-physical communication with one another. FIG. 8(e), f, g and h may be the turns of a single winding of a disrupting element or multiple disrupting elements and FIG. 8(h) represents a combination thereof with the disrupting element 26 physically separated from the turns 24 of a separate disrupting element.

It is noted that the disrupting elements may take various forms such as square, triangular, hexagonal or another shape that forms a closed loop when in use. Presented in FIG. 9 is an embodiment wherein the inner disrupting element comprises a solid circle or any other shape of metal. The induced currents mainly flow around the surface of the solid metal disc and therefore this disc acts in a similar manner to the previously described metal loops. By way of example presented in FIG. 9 is a half-moon metal shape that may be used to again tune the amount of near field cancellation. However it should further be noted that the disrupting elements have been described as passive however it is also possible that a current may be passed through the one or more disrupting elements to make the disruptive element(s) active which will further disrupt the magnetic field of the winding provided the current passed through in the correct direction. A further alternative may be that the turns of the winding be twisted back on itself and the turns continued in the opposite direction thereby creating a similar effect.

Referring to FIG. 10(a) presented is a peak magnetic field associated with a normal polarity coil arrangement comprising two windings of the formed as presented in FIG. 2(d). As presented in FIG. 10(b), the peak magnetic field can be seen to be significantly reduced as presented on the left hand side of the vertical axis compared to a normal double winding coil arrangement presented on the right hand side of the vertical axis. It will be appreciated that the reduction of peak magnetic field of this embodiment is not as large as utilising a reverse polarity arrangement however in this embodiment disrupting elements have been provided adjacent the core of each winding and also around substantially the entire peripheral edge of each individual winding meaning that the power input must be scaled (reduced) to compensate for the increase in sound. This therefore has an effect of reduction in the peak magnetic field.

Referring to FIGS. 11(a) and (b), a plan and perspective view of a coil arrangement according to an exemplary embodiment of the present invention is presented with a single winding 4. First and second disrupting elements 10, 12 are provided and beneficially comprise an inner and an outer disrupting element positioned adjacent a radially inner edge of the winding and adjacent a radially outer edge of the winding respectively. FIG. 11(c) presents the peak magnetic field associated with a normal coil arrangement of single winding having no disrupting elements and can be compared to the corresponding peak magnetic field presented in FIG. 11(d) utilising the inner and outer disrupting elements 10, 12. A direct comparison is made in FIG. 11(e) clearly identifying the significant reduction in peak magnetic field. In FIG. 11(e) a normal coil arrangement having no disrupting elements and the peak magnetic field thereof is on the right hand side of the vertical axis and the peak magnetic field associated with the coil arrangement of FIGS. 11(a) and (b) is shown on the left hand side of the vertical axis.

Referring to FIG. 12 there is a schematic presentation of peak magnetic field provided from finite element method modelling for an embodiment of a coil arrangement for a normal coil arrangement on the right hand side presented by the identical rectangles which represent a cross section through the turns of the winding. On the left hand side as presented is a similar winding however, between the turns of the winding are provided unconnected conductive loops placed radially between the turns of the winding. The peak magnetic field can be seen to be hugely reduced utilising such a configuration.

Referring to FIG. 13 there is a further schematic perspective exemplary embodiment of the present invention. Presented in this embodiment are first and second windings 4, 6 wound in opposing clockwise and anti-clockwise directions. Importantly, however, in this embodiment the at least one disrupting element 10 is in position outside the generally common plane of the turns of the windings 4, 6. In the embodiment presented first 10 and second 12 disrupting elements are provided wherein the second disrupting element 12 is nested within the first disrupting element. It will be appreciated that any number of disrupting elements may be provided. In this embodiment the treatment side is preferably underneath the disrupting elements 10, 12.

It will be appreciated that for clarity purposes the provision of a housing has not been shown in the exemplary embodiments presented. Referring therefore to FIG. 14a-d a housing has been presented with reference to the embodiment of FIG. 13. A housing 60 may comprise a molding of two parts 60a, 60b forming a chamber 62 into which the winding(s) are housed as well as the one or more disrupting elements. In an alternative configuration the one or more windings and one or more disrupting elements may be potted and thus effectively encapsulated within a potting material.

Aspects of the present invention have been described by way of example only and it will be appreciated by the skilled addressee that modifications and variations may be made without departing from the scope of protection afforded by the appended claims.

The invention claimed is:

1. A magnetic stimulation (MS) coil arrangement comprising a radially wound conductive element having a plurality of turns forming at least one winding, the coil arrangement further including at least one elongate conductive magnetic field disrupting element at least partially positioned adjacent to the at least one winding for disrupting a magnetic field generated in operation by the at least one winding, the at least one elongate conductive magnetic field disrupting element arranged to attenuate the generated magnetic field beneath the coil arrangement, wherein the at least one elongate conductive magnetic field disrupting element comprises one of an inner disrupting element positioned adjacent a radially inner edge of the at least one winding and an outer disrupting element adjacent to a radially outer edge of one or more of the at least one winding, wherein the MS coil arrangement forms a sham or placebo MS coil arrangement, wherein the inner disrupting element follows a majority of the radially inner edge of one or more of the at least one winding and wherein the outer disrupting element follows a majority of the radially outer edge of one or more of the at least one winding.

2. A MS coil arrangement according to claim 1 wherein each of the at least one disrupting elements is a loop.

3. A MS coil arrangement according to claim 1 wherein the at least one elongate conductive magnetic field disrupting element is substantially non-magnetic.

4. A MS coil arrangement according to claim 1 wherein the at least one elongate conductive magnetic field disrupting element is non-ferromagnetic.

5. A MS coil arrangement according to claim 1 wherein the at least one elongate conductive magnetic field disrupting element is positioned such that current is induced therein by the generated magnetic field.

6. A MS coil arrangement according to claim 1 wherein the plurality of turns of the at least one winding lie in a generally common plane, and the at least one disrupting element lies at least partially in that plane.

7. A MS coil arrangement according to claim 1 wherein the at least one disrupting element comprises a first and at least one second disrupting elements.

8. A MS coil arrangement according to claim 1 comprising at least one of the at least one disrupting element positioned radially between adjacent turns of one or more of the at least one winding.

9. A MS coil arrangement according to claim 1 wherein the inner disrupting element adjacent a radially inner edge is substantially solid.

10. A MS coil arrangement according to claim 1 further comprising a neck portion extending from the at least one winding having a connector for connection to a power source, the at least one disrupting element terminating before the connector.

11. A MS coil arrangement according to claim 1 wherein the at least one disrupting element comprises a plurality of nested disrupting elements.

12. A MS coil arrangement according to claim 1 wherein the radially wound conducting element is formed into first and second windings of the at least one winding.

13. A MS coil arrangement according to claim 12 comprising a first magnetic field disrupting element of the at least one disrupting element adjacent the first winding and a second magnetic field disruptive element adjacent to the second winding.

14. A MS coil arrangement according to claim 13 wherein the first magnetic field disrupting element extends adjacent a portion of the radially inner edge of the first winding and the second magnetic field disrupting element extends adjacent a portion of the radially inner edge of the second winding, wherein the first and second disrupting elements positioned adjacent the first and second windings comprises a third conductive magnetic field disrupting element extending at least partially adjacent a radially outer edge of the first and the second windings.

15. A MS coil arrangement according to claim 12 comprising at least one of the at least one disrupting element at least partially positioned adjacent the first and second winding.

16. A MS coil arrangement according to claim 15 wherein the plurality of turns of the first winding lie in a generally common first plane, and the at least one elongate conductive magnetic field disrupting element lies at least partially in the first plane, and the second winding lies in a generally common second plane, and the at least one elongate conductive magnetic field disrupting element lies at least partially in the second plane.

17. A MS coil arrangement according to claim 16 wherein the first plane and second plane are substantially the same.

18. A MS coil arrangement according to claim 12 wherein the turns of the radially wound conductive element are wound clockwise or counter-clockwise for both the first and the second winding.

19. A MS coil arrangement according to claim 1 wherein the at least one winding and at least one elongate conductive magnetic field disrupting element are provided in a housing.

20. A MS coil arrangement according to claim 19 wherein the housing comprising a potting material.

21. A magnetic stimulation (MS) coil arrangement comprising a radially wound conductive element having a plurality of turns forming at least one winding, the coil arrangement further including a plurality of conductive magnetic field disrupting elements at least partially positioned adjacent the at least one winding for disrupting a magnetic field generated in operation by the at least one winding, the conductive magnetic field disrupting elements arranged to attenuate the generated magnetic field beneath the coil arrangement to form a sham or placebo MS coil arrangement, wherein each of the plurality of conductive magnetic field disrupting elements comprises an inner disrupting element positioned adjacent a radially inner edge of the at least one winding and/or an outer disrupting element adjacent to a radially outer edge of one or more of the at least one winding.

22. A MS coil arrangement according to claim 21 wherein the plurality of turns lie in a generally common plane, and the first and second disrupting elements lie at least partially in that plane.

23. A MS coil arrangement according to claim 22 wherein the first and the second disrupting elements are radially spaced by one or more turns of the at least one winding.

24. A MS coil arrangement according to claim 21 wherein the first and optionally the second conductive magnetic field disrupting element is elongate.

25. A MS coil arrangement according to claim 21 wherein the first and optionally the second conductive magnetic field disrupting elements are loops.

26. A MS coil arrangement according to claim 21 wherein the first conductive magnetic field disrupting element is adjacent a radially outer edge of the at least one winding.

27. A MS coil arrangement according to claim 21 wherein the second conductive magnetic field disrupting element is adjacent a radially inner edge of the at least one winding.

28. A magnetic stimulation (MS) coil arrangement comprising a radially wound conductive element having a plurality of turns in a substantially common plane forming at least one winding, the coil arrangement further including a conductive magnetic field disrupting element at least partially positioned adjacent the at least one winding and being at least partially disposed to lie in the substantially common plane for disrupting a magnetic field generated in operation by the at least one winding, the conductive magnetic field disrupting element arranged to attenuate the generated magnetic field beneath the coil arrangement to form a sham or placebo MS coil from the MS coil arrangement, wherein the conductive magnetic field disrupting element comprises an inner disrupting element positioned adjacent a radially inner edge of the at least one winding and/or an outer disrupting element adjacent to a radially outer edge of one or more of the at least one winding, wherein the inner disrupting element follows a majority of the radially inner edge of one or more of the at least one winding and wherein the outer disrupting element follows a majority of the radially outer edge of one or more of the at least one winding.

29. A MS coil arrangement according to claim 28 comprising a Transcranial Magnetic Stimulation (TMS) coil arrangement.

30. A method of attenuating the magnetic field generated in operation by a magnetic stimulation (MS) coil arrangement comprising a radially wound conductive element having a plurality of turns forming at least one winding and an elongate conductive magnetic field disrupting element positioned at least partially adjacent to the at least one winding, and passing a current through the at least one winding, wherein the elongate conductive magnetic field disrupting element attenuates the magnetic field beneath the MS coil arrangement to form a sham or placebo MS coil from the MS coil arrangement, wherein the elongate conductive magnetic field disrupting element comprises an inner disrupting element positioned adjacent a radially inner edge of the at least one winding and/or an outer disrupting element adjacent to a radially outer edge of one or more of the at least one winding, wherein the inner disrupting element follows a majority of the radially inner edge of one or more of the at least one winding and wherein the outer disrupting element follows a majority of the radially outer edge of one or more of the at least one winding.

* * * * *